United States Patent
Jackson

(10) Patent No.: US 9,585,701 B2
(45) Date of Patent: Mar. 7, 2017

(54) BONE ANCHOR CONFIGURED TO ANCHOR AN ELONGATED IMPLANT TO A PATIENT BONE

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

(21) Appl. No.: 14/245,660

(22) Filed: Apr. 4, 2014

(65) Prior Publication Data
US 2014/0222090 A1    Aug. 7, 2014

Related U.S. Application Data

(60) Continuation of application No. 13/573,660, filed on Oct. 2, 2012, now Pat. No. 9,055,978, which is a continuation of application No. 13/374,932, filed on Jan. 24, 2012, now Pat. No. 8,377,067, which is a continuation of application No. 12/584,413, filed on
(Continued)

(51) Int. Cl.
*A61B 17/70* (2006.01)
*A61B 17/56* (2006.01)

(52) U.S. Cl.
CPC ...... *A61B 17/7085* (2013.01); *A61B 17/7001* (2013.01); *A61B 17/7002* (2013.01); *A61B 17/7011* (2013.01); *A61B 17/7032* (2013.01); *A61B 17/7035* (2013.01); *A61B 17/7037* (2013.01); *A61B 17/7088* (2013.01); *A61B 17/7091* (2013.01); *A61B 2017/564* (2013.01)

(58) Field of Classification Search
CPC ............ A61B 17/7032; A61B 17/7035; A61B 17/7037; A61B 17/7038; A61B 17/704; A61B 17/7046

USPC .................................................. 606/264–279
See application file for complete search history.

(56) References Cited

U.S. PATENT DOCUMENTS

| 6,077,262 A | 6/2000 | Schlapfer et al. |
| 6,139,549 A | 10/2000 | Keller |

(Continued)

FOREIGN PATENT DOCUMENTS

| DE | 20207850 U1 | 10/2002 | |
| WO | WO 95/13755 | 5/1995 | |
| WO | WO 03/028566 A1 * | 4/2003 | ......... A61B 17/7032 |

OTHER PUBLICATIONS

European Search Report, EP14189707.4, dated Feb. 25, 2015.

*Primary Examiner* — Mary Hoffman
(74) *Attorney, Agent, or Firm* — Polsinelli PC

(57) ABSTRACT

A tool set for implanting a rod in a human spine in conjunction with bone screws. The tool set includes a pair of end guide tools that receive opposite ends of the rod in channels and under manipulation by a surgeon facilitate transport of the rod toward the bone screws attached to the guide tools. Intermediate guide tools having guiding pass through slots are utilized to guide intermediate locations along the rod toward associated bone screws. An attachment structure operably connects the guide tools to the bone screws. The guide tools each include a lower guide and advancement structure to allow a closure top with mating structure to be rotated and driven downward against the rod and to cooperate with similar structure in the bone screw to seat and lock the rod therein. A method utilizing the tool set allows a surgeon to percutaneously implant the rod in the patient.

19 Claims, 13 Drawing Sheets

Related U.S. Application Data

Sep. 4, 2009, now Pat. No. 8,100,915, which is a continuation of application No. 12/220,185, filed on Jul. 22, 2008, now Pat. No. 8,162,948, which is a division of application No. 10/789,149, filed on Feb. 27, 2004, now Pat. No. 7,160,300.

(56) References Cited

U.S. PATENT DOCUMENTS

| | | |
|---|---|---|
| 6,440,133 B1 | 8/2002 | Beale et al. |
| 6,530,929 B1 | 3/2003 | Justis et al. |
| 6,648,888 B1 | 11/2003 | Shluzas |
| 6,730,089 B2 | 5/2004 | Jackson |
| 6,932,822 B2 | 8/2005 | Oribe et al. |
| 7,160,300 B2 | 1/2007 | Jackson |
| 7,179,261 B2 | 2/2007 | Sicvol et al. |
| 7,250,052 B2 | 7/2007 | Landry et al. |
| 7,527,638 B2 | 5/2009 | Anderson et al. |
| 7,547,318 B2 | 6/2009 | Birkmeyer et al. |
| 7,666,188 B2 | 2/2010 | Anderson et al. |
| 7,708,763 B2 | 5/2010 | Selover et al. |
| 8,066,739 B2 | 11/2011 | Jackson |
| 8,100,915 B2 | 1/2012 | Jackson |
| 8,162,948 B2 | 4/2012 | Jackson |
| 8,377,067 B2 | 2/2013 | Jackson |
| 9,101,415 B2 | 8/2015 | Jackson |
| 2002/0143341 A1 | 10/2002 | Biedermann et al. |
| 2003/0023240 A1 | 1/2003 | Amrein et al. |
| 2003/0100904 A1 | 5/2003 | Biedermann |
| 2003/0167058 A1* | 9/2003 | Shluzas .................. 606/61 |
| 2005/0216003 A1 | 9/2005 | Biedermann et al. |
| 2014/0222077 A1 | 8/2014 | Jackson |
| 2014/0236243 A1 | 8/2014 | Jackson |
| 2015/0080957 A1 | 3/2015 | Jackson |
| 2015/0080962 A1 | 3/2015 | Jackson |
| 2015/0080965 A1 | 3/2015 | Jackson |
| 2015/0150606 A1 | 6/2015 | Jackson |

* cited by examiner

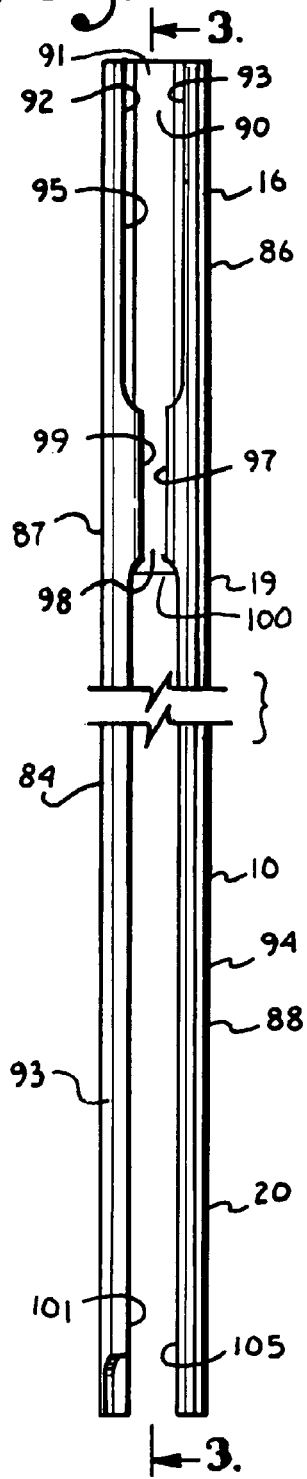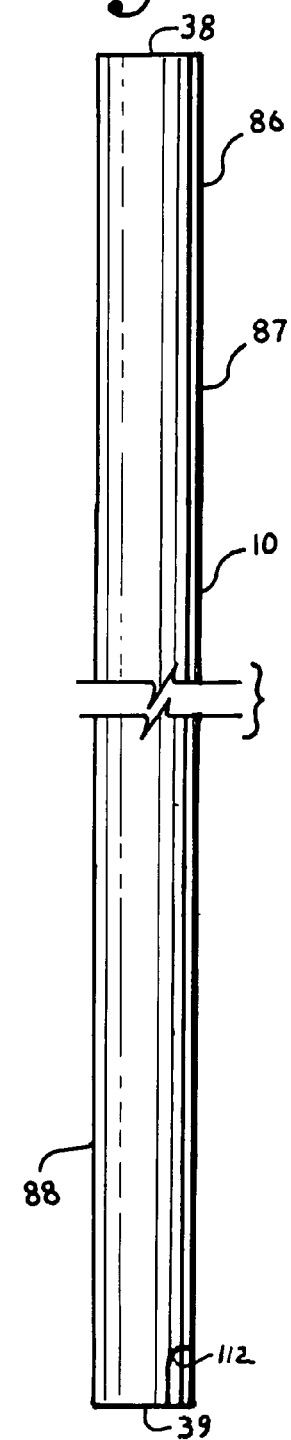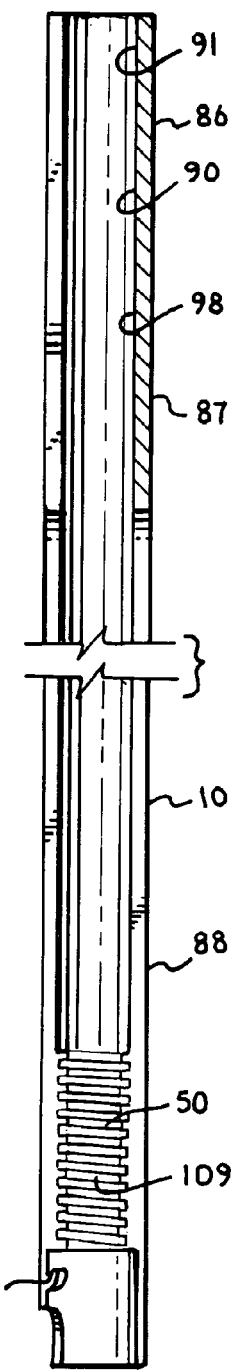

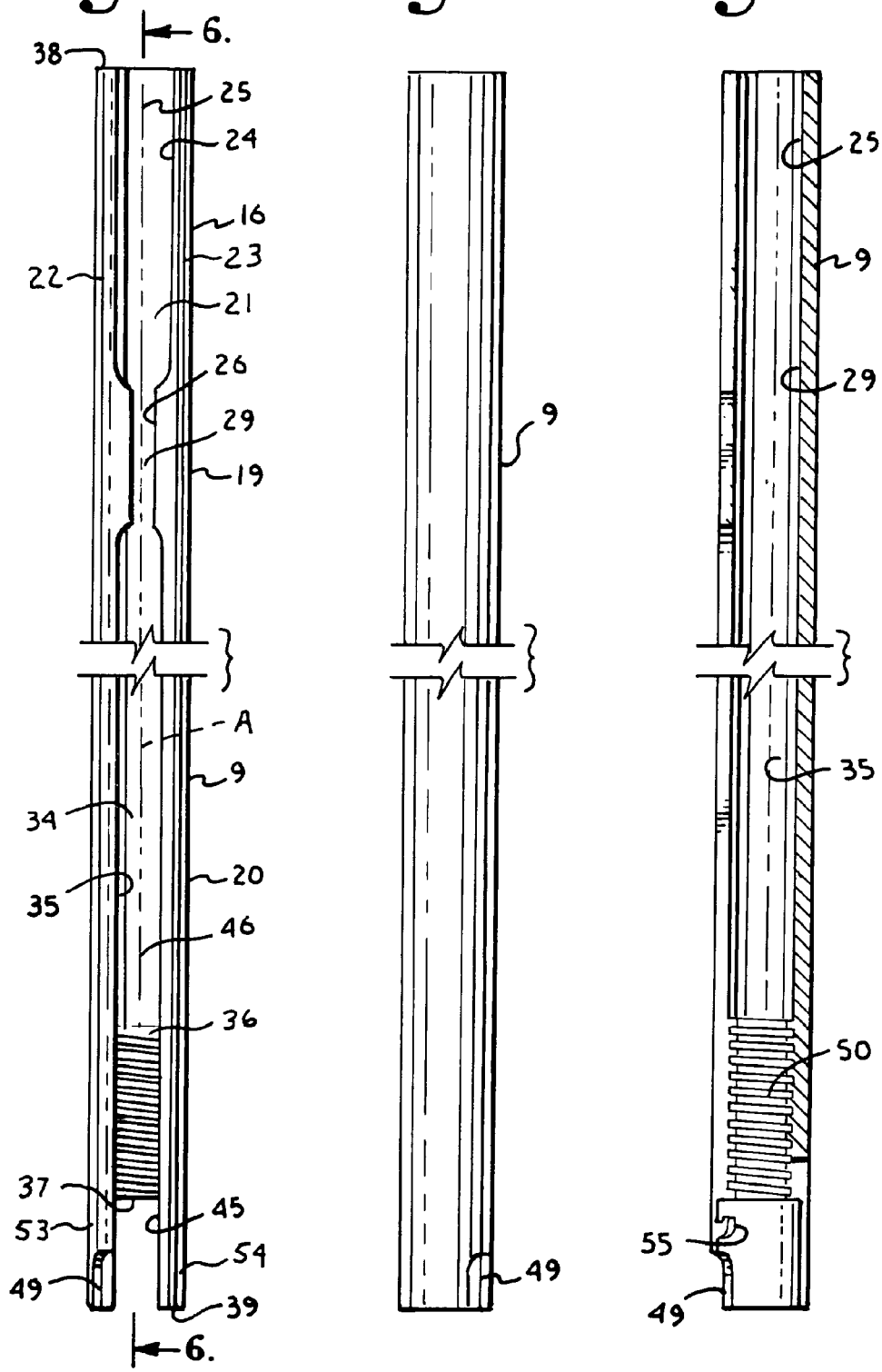

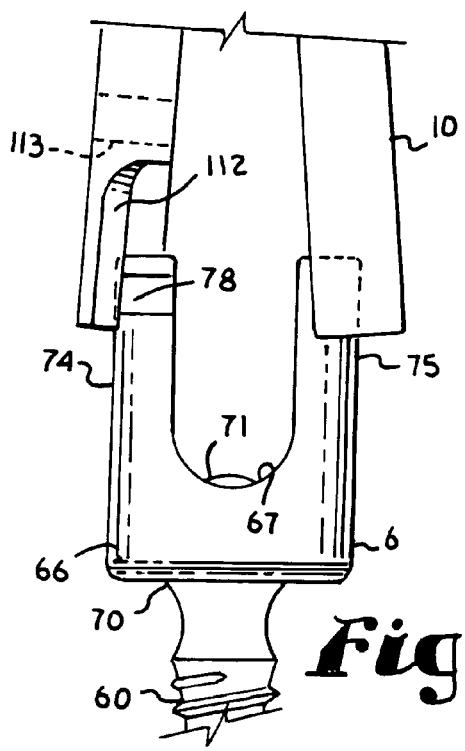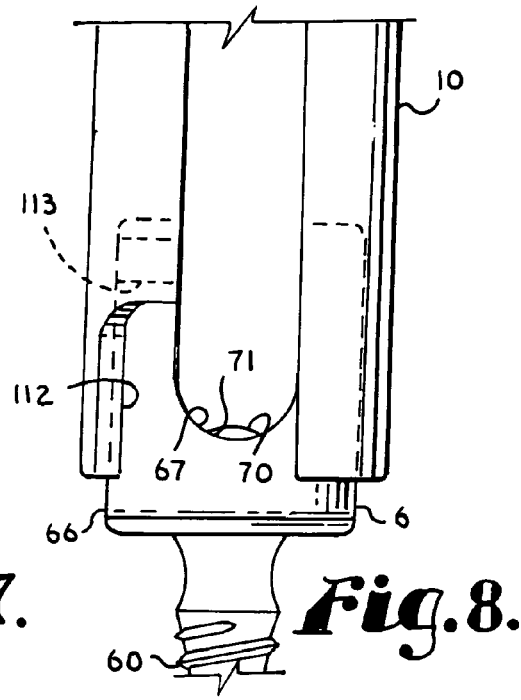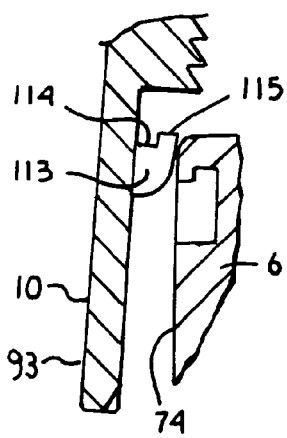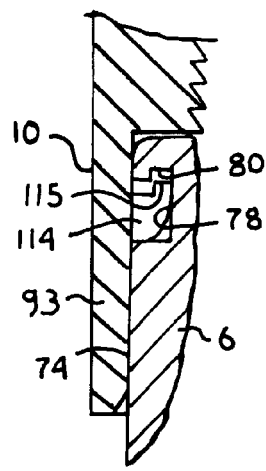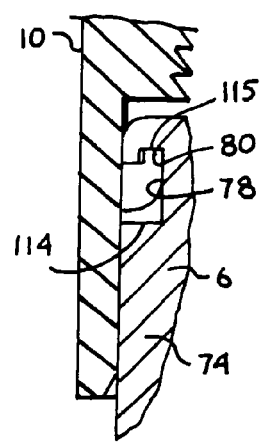

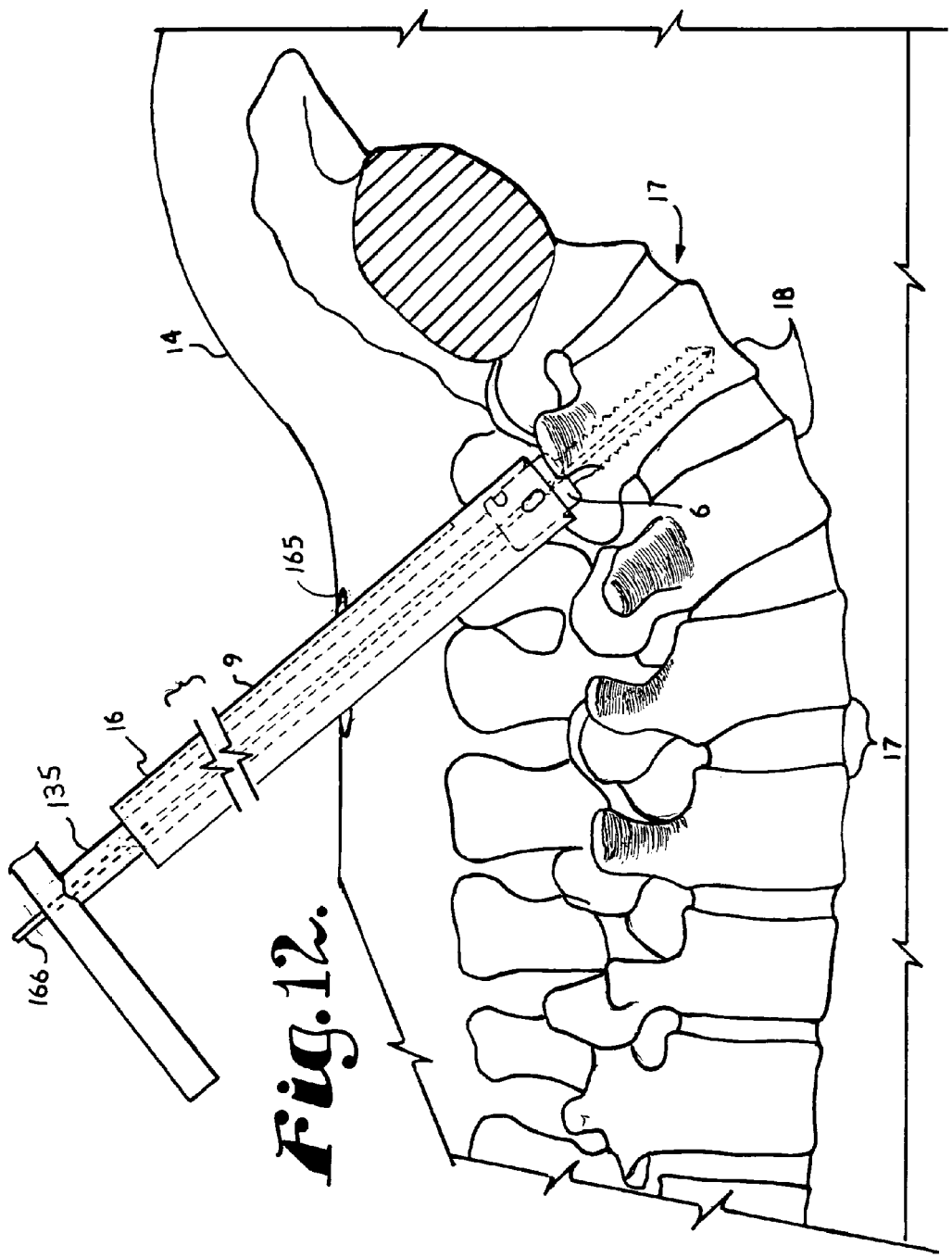

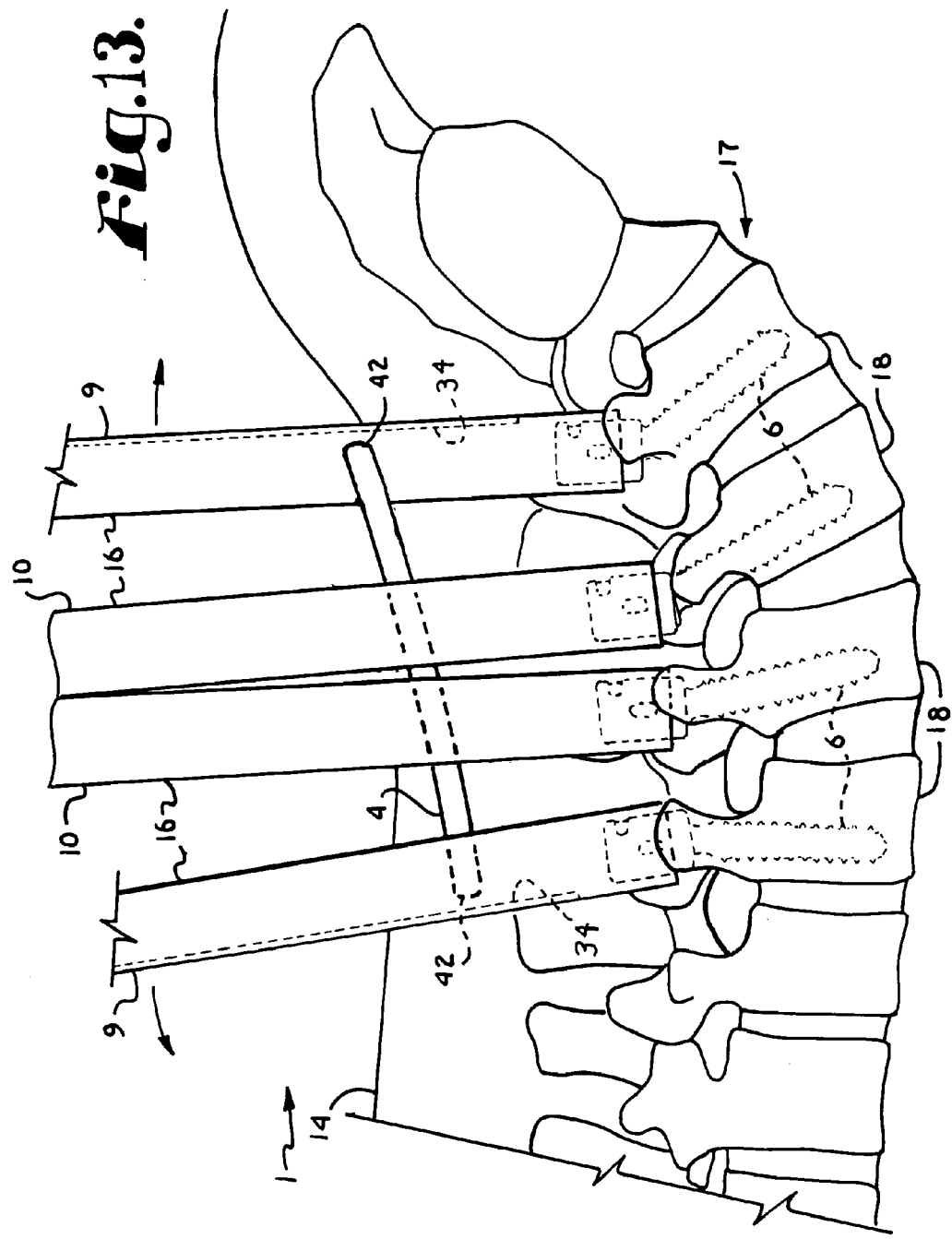

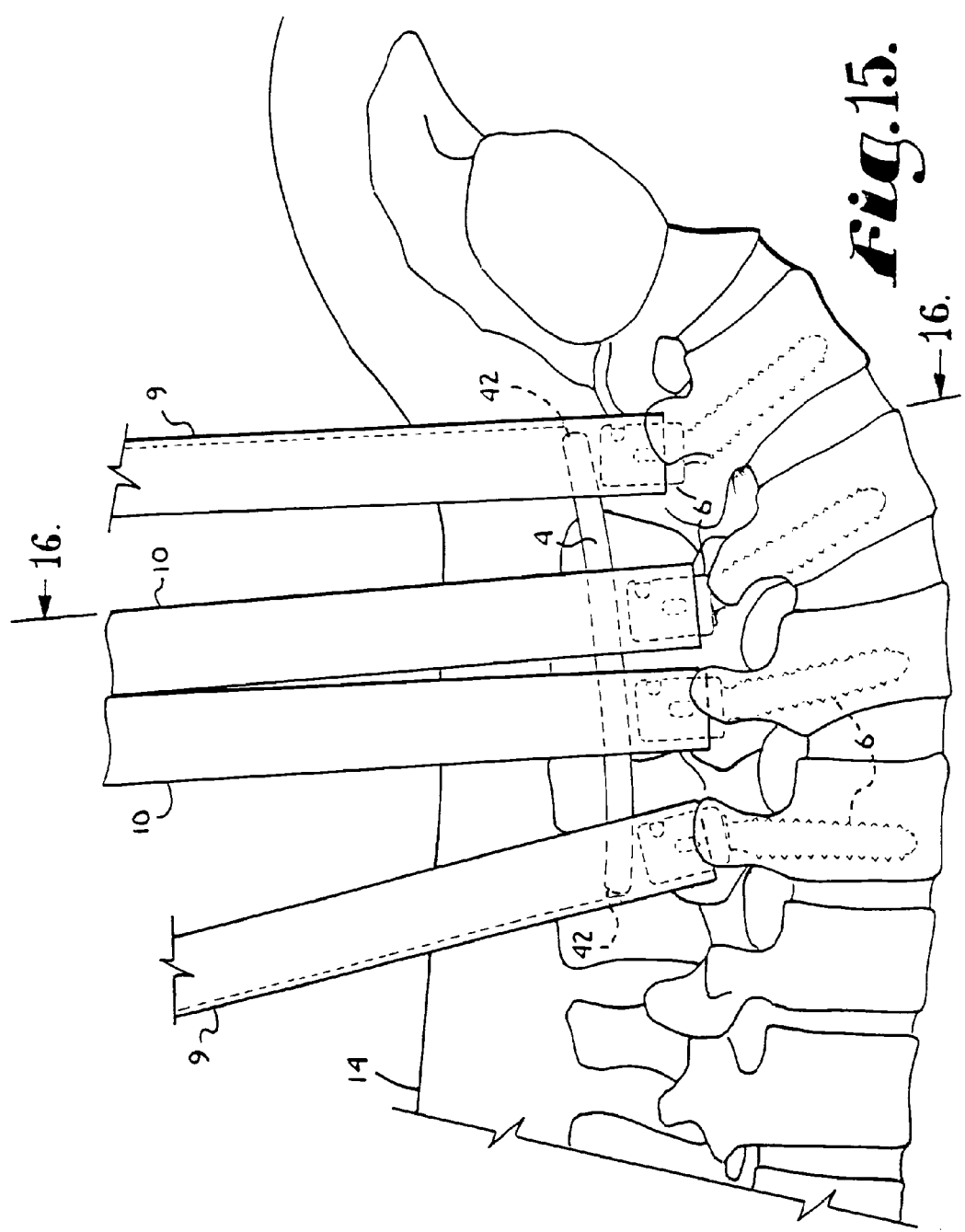

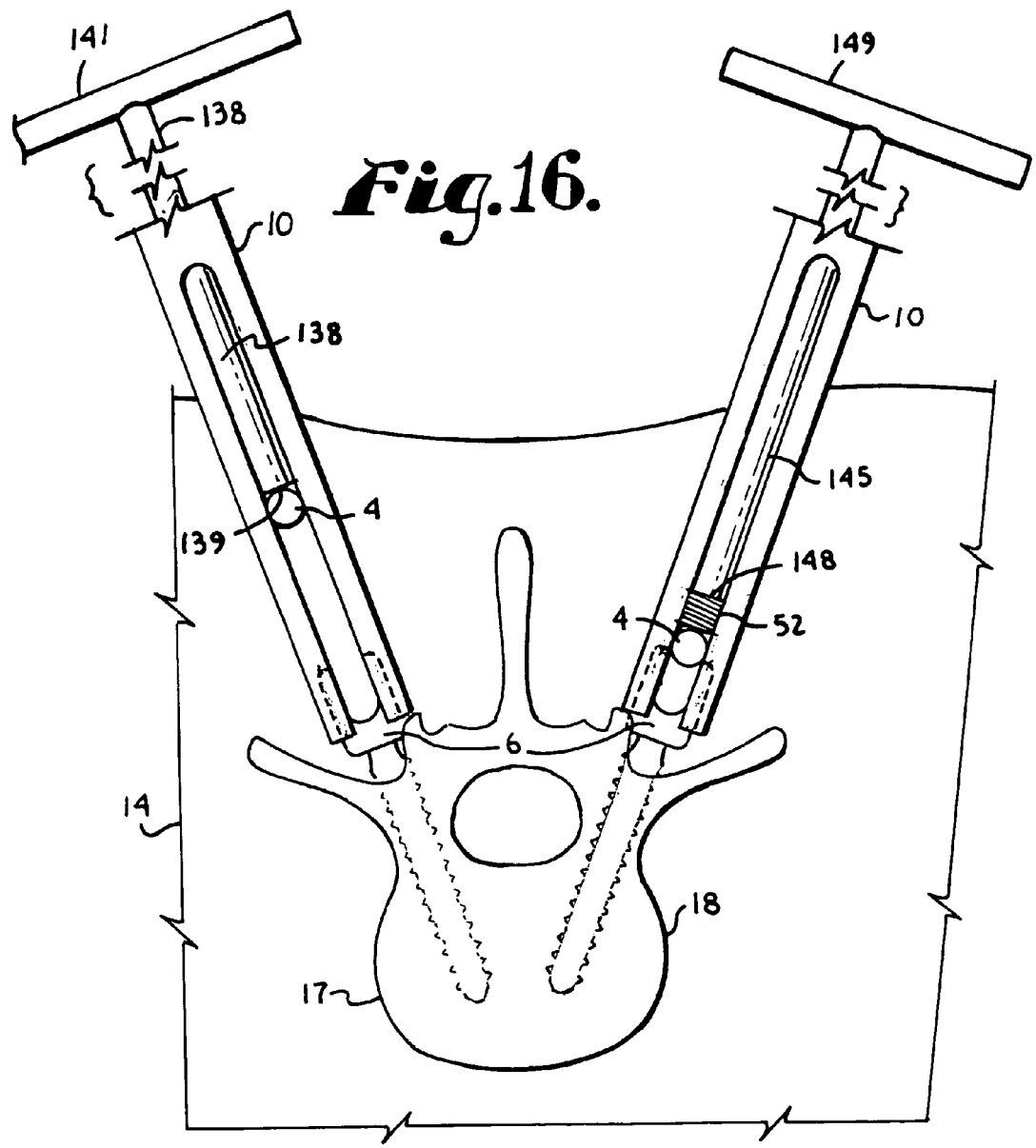

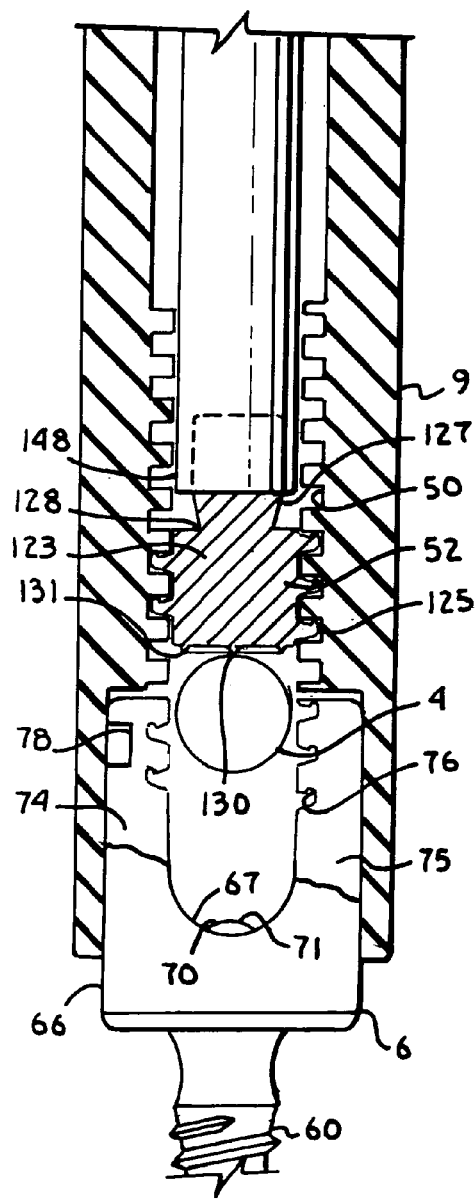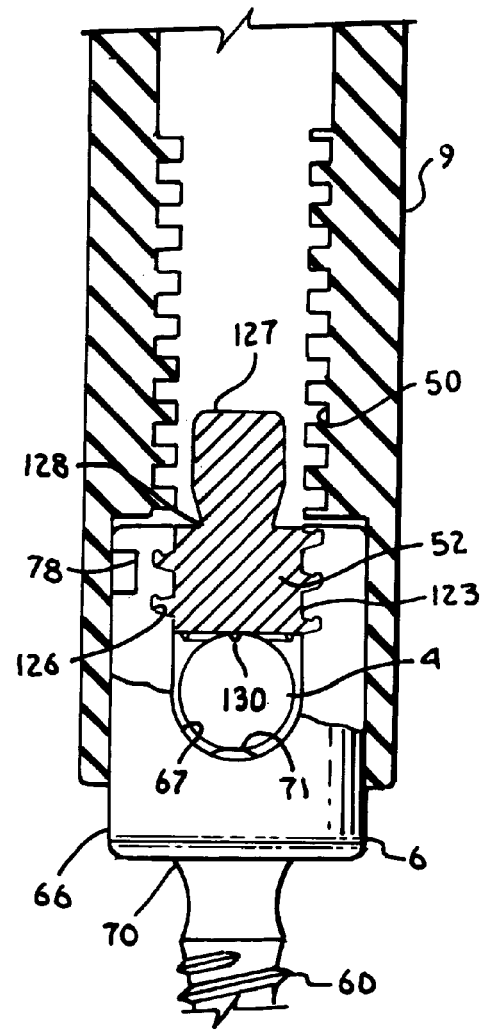

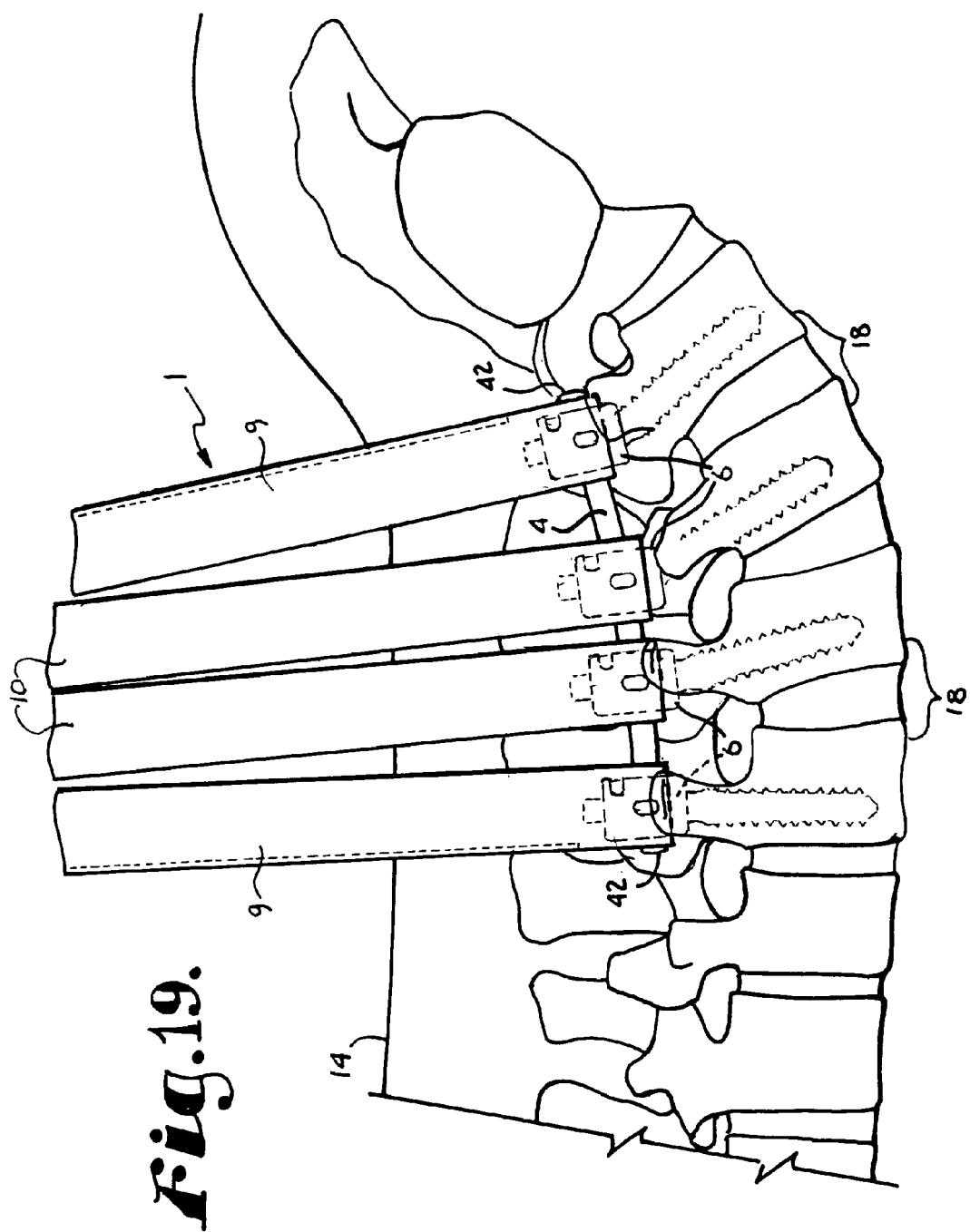

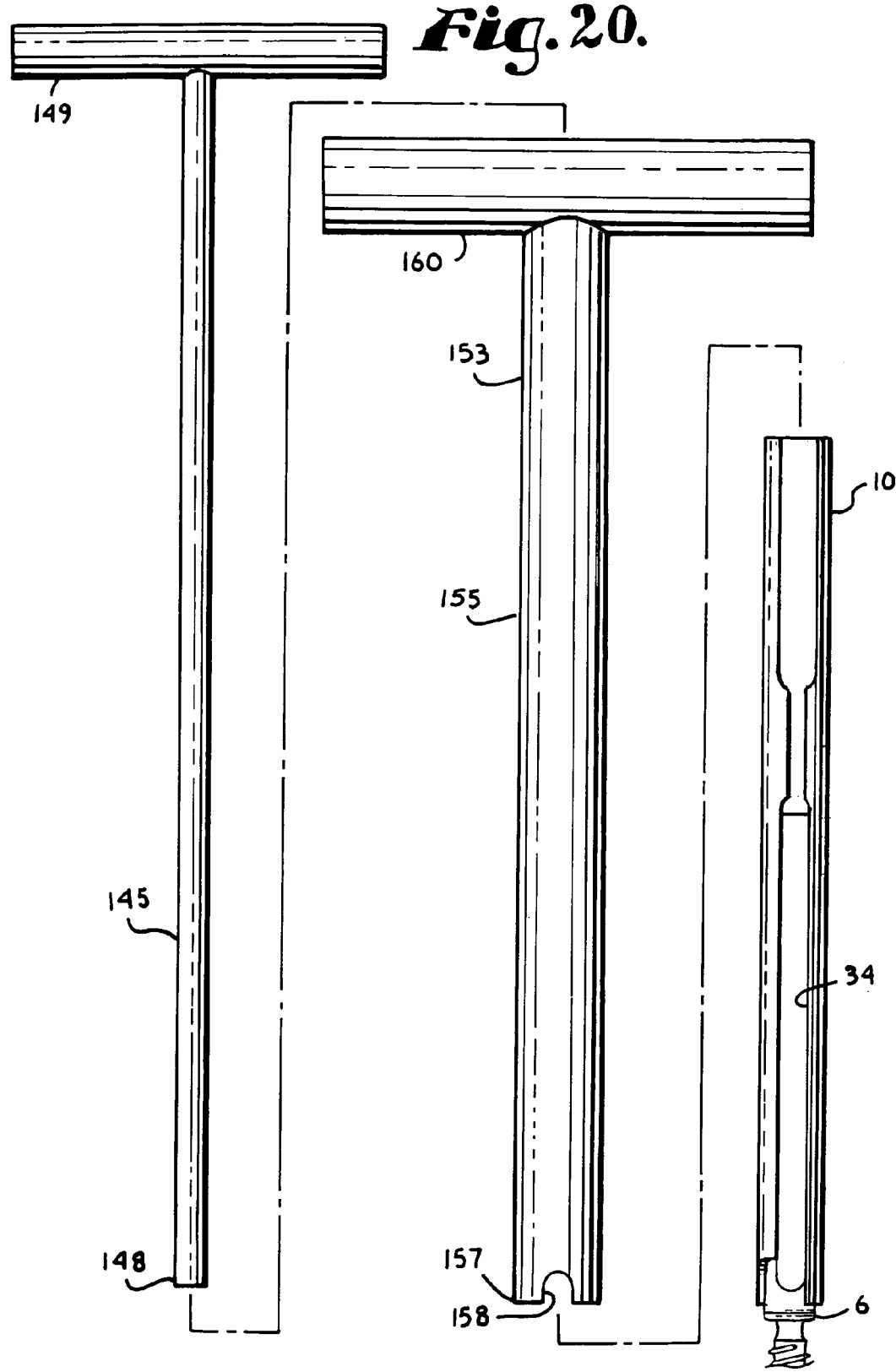

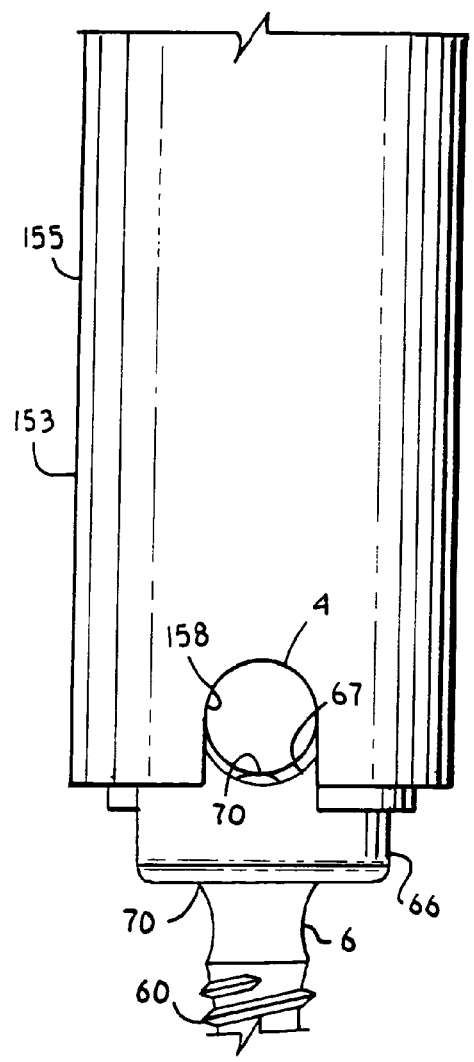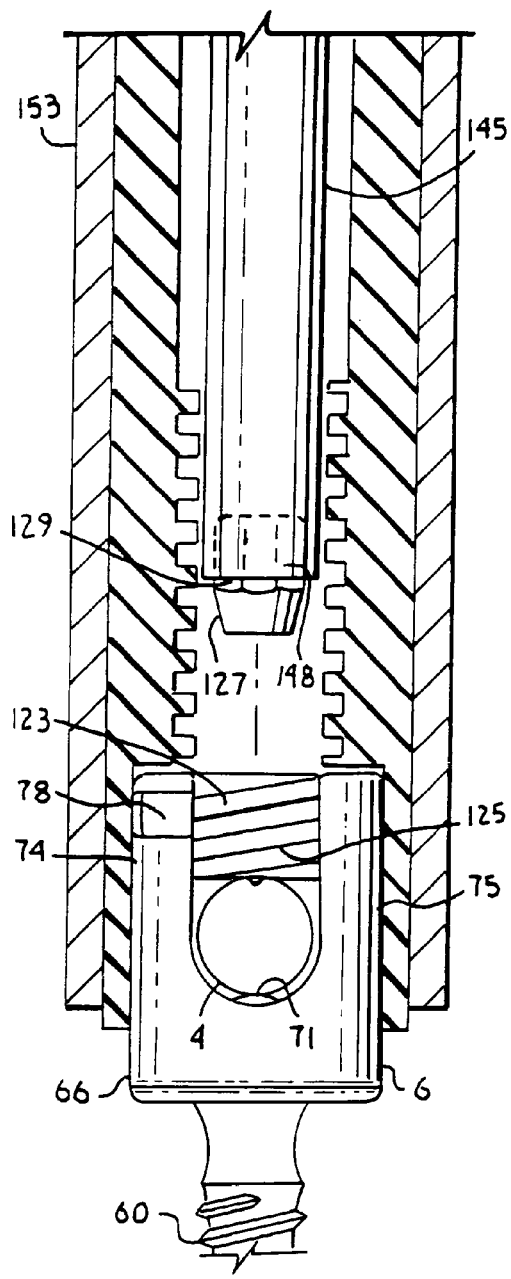

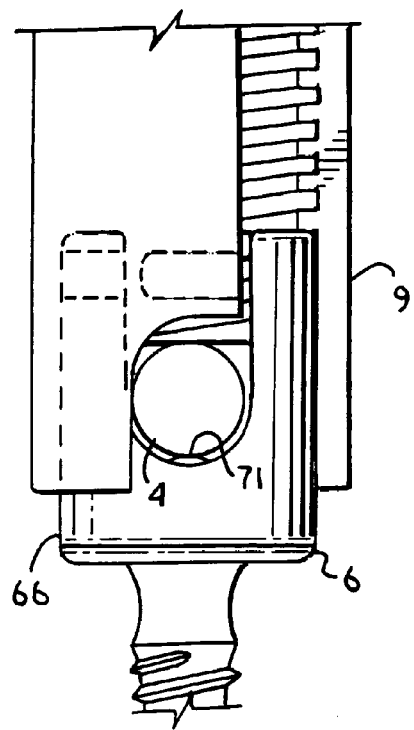
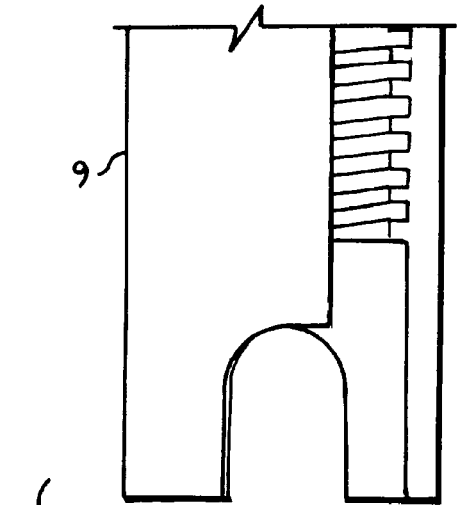
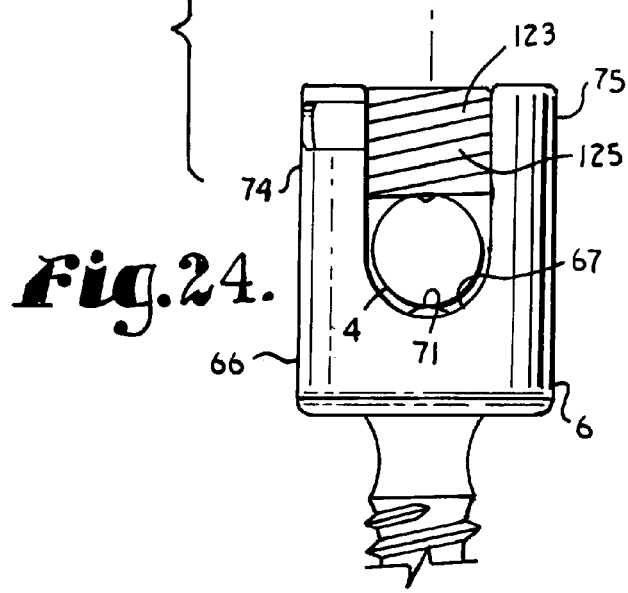
Fig.23.
Fig.24.

BONE ANCHOR CONFIGURED TO ANCHOR AN ELONGATED IMPLANT TO A PATIENT BONE

CROSS-REFERENCE TO RELATED APPLICATION

This application is a continuation of U.S. patent application Ser. No. 13/573,660 filed Oct. 2, 2012, which application is a continuation of U.S. patent application Ser. No. 13/374,932, filed Jan. 24, 2012, now U.S. Pat. No. 8,377,067 dated Feb. 19, 2013, which is a continuation of U.S. patent application Ser. No. 12/584,413, filed Sep. 4, 2009, now U.S. Pat. No. 8,100,915 dated Jan. 24, 2012, which is a continuation of U.S. patent application Ser. No. 12/220,185, filed Jul. 22, 2008, now U.S. Pat. No. 8,162,948 dated Apr. 24, 2012, which is a division of U.S. patent application Ser. No. 10/789,149, filed Feb. 27, 2004, which issued as U.S. Pat. No. 7,160,300 on Jan. 9, 2007, all of which are incorporated herein by reference.

BACKGROUND OF THE INVENTION

The present invention relates to apparatuses and methods for use in performing spinal surgery and, in particular, to tools and methods of using such tools, especially for percutaneously implanting a rod for spinal support and alignment using minimally invasive techniques.

For many years, spinal osteosynthesis apparatuses have been utilized to correct spinal deformities, injuries or disease. In such procedures, elongate rods are surgically attached to vertebrae of the spine to provide support and/or to reposition certain vertebrae. Such rods are secured to vertebrae utilizing bone screws and other implants.

Surgical techniques and bone screws have improved; however, in order to reduce the impact of such surgery on the patient, it has been desirable for such implants to be inserted percutaneously or with surgical techniques that are minimally invasive to the body of the patient. This presents a problem with implantation of rods that are elongate and have historically required a long incision and open wound in order to provide for the length of the rod and the space required for the surgeon's hands to manipulate the rod, implants and insertion tools used with the rod. Consequently, it has been desirable to develop apparatuses and techniques that allow for the insertion of bone screws, the insertion and reduction of a rod and the securing of the rod to the bone screws with significantly reduced invasion into the body of the patient and with minimal incision size in the skin over the operational site.

SUMMARY OF THE INVENTION

A set of tools is provided for percutaneously implanting a spinal rod in a patient. The tools include a pair of end guide tools that have channels sized to receive opposite ends of such a rod and allow sliding of the rod along the channel so as to guide ends of the rod into opposed end bone screwheads to which the end guide tools are attached. Intermediate guide tools are also attached to bone screw-heads between the end bone screws and are slotted to guide the rod to respective bone screws attached to the intermediate guide tools.

The guide tools also include lower attachment structure to allow the guide tools to be easily and quickly secured to mating structure on a respective bone screw-head, and to be easily removed from the bone screw by manual rotation of a handle of the tools exterior of the patient, after which the guide tool is withdrawn from the patient. The intermediate guide tools have a snap-on and twist-off association with an associated intermediate bone screw and the end guide tools have a twist-on and twist-off association with respective end bone screws. In certain embodiments, other attachment structure may be used.

Each of the guide tools also includes an internal first lower guide and advancement structure that functions in cooperation with an internal second guide and advancement structure within the bone screw head and also with external helical wound thread or locking flange form mating structure on a bone screw closure top for closing the head of the bone screw, so as to be able to load the closure top though a top-to-bottom passageway in the guide tool and rotate the closure top with a closure top installation tool. Beneath the surface of the skin, the closure top is partially surrounded by the guide tool as it is directed to the bone screw. Clockwise rotation of the closure top in the region of the lower guide and advancement structure engages the closure top therewith and produces mechanical advantage that causes the closure top to be driven against the rod as it advances thereby urging the rod into the head of a respective bone screw. The closure top is driven and advanced by rotation of the closure top by the closure top installation tool and transferred or passed from the first guide and advancement structure in the guide tool to the second guide and advancement structure in the bone screw without losing mechanical advantage and while continually applying downward pressure on the rod, so as to drive the closure top downward and against the rod and so as to bias the rod into the head of the bone screw where it is captured by the closure top and locked in position.

OBJECTS AND ADVANTAGES OF THE INVENTION

Therefore, the objects of the present invention are: to provide a set of tools for implanting a spinal rod for support or alignment along a human spine with minimal surgical invasion of the patient; to provide such a set of tools including a pair of end tool guides for slidably guiding opposed ends of the rod toward end bone screws attached to the end guide tools; to provide such a set of tools including intermediate guide tools for each intermediate bone screw that guide the rod in slots therethrough to respective bone screws; to provide such a set of tools including rod pusher and closure top installation tools for assisting in securing the rod in the bone screws; to provide such a set of tools where the end guide tools include a longitudinal channel extending upwardly from near a bottom thereof to slidingly receive and guide ends of the rod toward associated end bone screws; to provide such a set of tools wherein the guide tools are easily attached to and disengaged from the bone screws; to provide such a set of tools wherein each guide tool includes a first guide and advancement structure near the bottom thereof that receives thread or locking flange mating structure on the closure top and advances the closure top upon rotation of the closure top to urge the rod downwardly; to provide such a set of tools wherein the guide tool first guide and advancement structure acts cooperatively with a second guide and advancement structure on the bone screw so as to transfer the closure top upon rotation thereof from the guide tool to the bone screw while continuously applying pressure to the rod and thereafter further advance the closure top to urge the rod into a seated position in the bone screw; to provide such a set of tools wherein the guide tools easily attach to and disengage from the bone screws by manual manipulation of the surgeon outside the patient's skin; to provide a method of implanting a rod into a patient with minimal surgical invasion of the patient; to provide such a method utilizing the previously described tools for percutaneous implantation of such a rod; to provide such a method wherein end guide tools are utilized to receive opposite ends of a rod and guide the rod ends in the guide tool channels through manipulation of the guide tools and use of rod pusher tools; to provide such a method wherein intermediate guide tools are utilized to guide intermediate locations along the rod to respective intermediate bone screws; to provide such a method wherein guide and advancement structure near the bottoms of the guide tools, on the bone screws and on the closure tops are utilized to pass the closure top under rotation and with driving force between the guide tools and the bone screws and to drive the rod into a seating position in the bone screw; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary front elevational view of an intermediate guide tool in accordance with the present invention.

FIG. 2 is a fragmentary side elevational view of the intermediate guide tool.

FIG. 3 is a fragmentary cross sectional view of the intermediate guide tool, taken along line 3-3 of FIG. 1.

FIG. 4 is a fragmentary front elevational view of an end guide tool.

FIG. 5 is a fragmentary side elevational view of the end guide tool.

FIG. 6 is a cross sectional view of the end guide tool, taken along line 6-6 of FIG. 4.

FIG. 7 is an enlarged and fragmentary front elevational view showing snap-on installation of the intermediate guide tool on a polyaxial bone screw head.

FIG. 8 is an enlarged and fragmentary front elevational view showing the intermediate guide tool installed on the bone screw head.

FIG. 9 is a fragmentary and cross-sectional view showing an early stage of the snap on installation of the intermediate guide tool on the bone screw head.

FIG. 10 is a fragmentary and cross-sectional view showing a later stage of installation of the intermediate guide tool on the bone screw head.

FIG. 11 is a fragmentary and cross-sectional view showing the intermediate guide tool installed on the bone screw head.

FIG. 12 is a partial and generally schematic view of a patient's spine with the end guide tool in conjunction with a bone screw installation tool, at the end of a process of installing a bone screw with attached end guide tool in a spinal vertebra.

FIG. 13 is a partial and generally schematic view of the spine with a pair of end guide tools and a pair of intermediate guide tools mounted on respective implanted bone screws and being utilized in an early stage of rod implantation to guide the rod toward the bone screws.

FIG. 15 is a view similar to FIG. 13 showing a later intermediate stage of guiding the rod toward the bone screws.

FIG. 16 is a partial and generally schematic cross sectional view of the spine showing rods being implanted on opposite sides of the spine and with the rod on the left in an early stage of implanting while the rod on the right is in a later stage of implanting, taken along line 16-16 of FIG. 15.

FIG. 17 is a cross-sectional view of an end guide tool, similar to FIG. 6, shown during installation of the rod and a closure top in the bone screw attached to the end guide tool.

FIG. 18 is a view similar to FIG. 17 showing the rod and closure top installed in the bone screw before final torquing of the closure top.

FIG. 19 is a partial and generally schematic side view of the spine showing the rod fully installed in the bone screws.

FIG. 20 is an exploded and front elevational view of a closure top installation tool, antitorque tool and one of the intermediate guide tools attached to a bone screw.

FIG. 21 is a fragmentary and front elevational view of the antitorque tool being positioned so as to allow final torquing to a closure top in the bone screw.

FIG. 22 is an enlarged and fragmentary side view of the end guide tool, as shown in FIG. 21, in conjunction with the installation tool and antitorque tool with portions broken away to shown interior detail and with the closure top having just been installed and torqued in the bone screw so that a break away head of the closure top has been removed.

FIG. 23 is a fragmentary and enlarged front elevational view showing an early stage in the removal of the end guide tool from the bone screw wherein the tool has been rotated approximately ninety degrees relative to its axis to the shown removal configuration from the installation configuration, such as seen in FIG. 17, thereof.

FIG. 24 is a fragmentary and enlarged front elevational view showing the end guide tool disengaged from the bone screw.

DETAILED DESCRIPTION OF THE INVENTION

Figure 14:
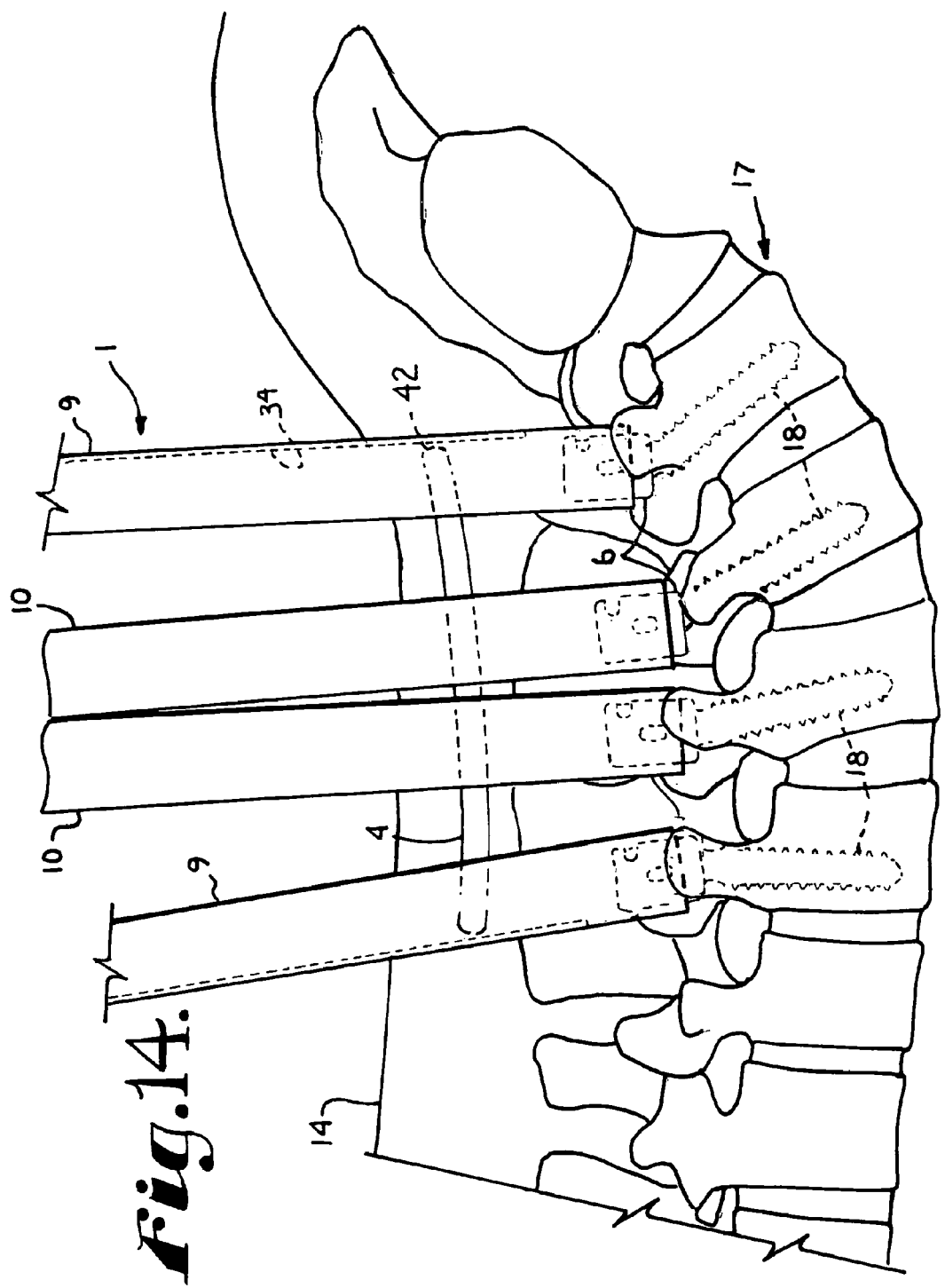
FIG. 14 is a view similar to FIG. 13 showing an intermediate stage of guiding the rod toward the bone screws.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a tool set for use in installing an orthopedic spinal rod 4 into a set of bone screws 6 in accordance with the present invention.

The tool set 1 of the illustrated embodiment includes a pair of end guide tools 9 and a plurality of intermediate guide tools 10, which in the illustrated embodiment includes a pair of intermediate guide tools 10 on each side of a patient's spine 17, but which can include none, one or many intermediate guide tools 10 depending upon the particular application, so that one intermediate guide tool 10 is used for each intermediate bone screw 6 to which the rod 4 is to be attached. The bone screws 6 are implanted in the patient's spine 17 and, in particular, in vertebrae 18 along the spine 17. Rods 4 are often installed on both sides of the spine 17, as seen in FIG. 16, during the same procedure.

The end guide tool 9 is illustrated in FIGS. 4 through 6. In particular, each end guide tool 9 has an elongate body 14 that is sized and shaped to be sufficiently long to extend from implanted bone screws 6 through an exterior of a patient's skin 14 so as to provide an outwardly extending and upper handle portion 16 that allows and provides for gripping by a surgeon during procedures utilizing the tool set 1. Each of the end guides 9 include an intermediate portion 19 and a lower portion 20 along the length thereof. Each end guide tool 9 has a back wall 21 joining a pair of side walls 22 and 23.

More specifically, the upper portion 16 of each end guide tool 9 is generally channel shaped having a U-shaped cross-section, a C-shaped cross-section, a crescent shaped cross-section or the like in order to form an opening 24 that opens into and forms part of a channel 25 that opens radially to one side of the end guide tool 9 and defines the side to side opening 24 that is sufficiently wide to receive additional tools and/or a closure top, as will be discussed below. The intermediate portion 19 of each end guide also includes an outward facing channel 29 that has an opening 26 which is somewhat smaller than the opening 24 of the upper portion 16, such that the channel 29 is sized and shaped to receive certain tools, as described below. Finally, the end guide lower portion 20 also includes a groove or channel 34 opening radially outward and having a side-to-side width or opening 35 that is approximately the same size as the opening 26. The channel 34 has a rear web or wall 36 having a lower end 37. All of the channels 25, 29 and 34 communicate with one another and are aligned with one another so as to provide a continuous elongate interior passageway with an open side from near a top 38 to near a bottom 39 thereof. This passageway provides a continuous open path of non uniform cross-section radius from the top 38 to the bottom 39 thereof that is parallel to an elongate axis A of each end guide tool 9. As will be discussed later, each end guide tool channel 34 is especially sized and shaped to slidingly receive a respective end 42 of the rod 4 therein.

Near the end guide bottom 39 is a cut out 45 wherein a portion of the back wall 21 of the channel 34 is removed in order to provide a region having a size and shape to allow passage of a respective end 42 of the rod 4 therethrough. Also located near the end guide bottom 39 is a rod abutment recess 49 that is sized and shaped for the purpose of bridging the rod 4 when the end guide tool 9 is rotated for removal, as described below. The end guide tool 9 also receives a closure top 52, as will be described below. Still further, near the bottom 39 of each of the end guides 9 is a helical wound first guide and advancement structure 50 which may include conventional helical threads, helically wound square threads, or other guide and advancement structure to cooperate with equivalent or mateable structure within the bone screw heads 6 and on the closure top 52, as also described below. The lower free ends of the side walls 22 and 23 form spaced tangs or legs 53 and 54.

At the bottom 39 of each end guide tool 9 is a radially inward facing attachment structure 55 that includes a base 56 and an upperly and axially extending projection, flange or hook member 57 which will be described in conjunction with a bone screw 6 below.

Referring more specifically to the bone screw 6, each of the bone screws 6 includes a threaded shank 60 for screwing into and seating in a vertebra 18 that is part of the human spine 17, see FIG. 12. Each of the bone screws 6 also include a head 66 with a rod receiving channel 67 passing therethrough. Each of the bone screw shanks 60 includes an upper portion 70 that extends into the head 66 and is operationally secured therein, so that the head 66 is rotatable on the shank 60 until locked in position through engagement with the rod 4 under pressure. In particular, each shank upper portion 70 has an upwardly extending dome 71 that engages the rod 4, when the rod 4 is placed within an associated channel 67 so that as the rod 4 urges the dome 71 downwardly, the shank upper portion 70 frictionally locks the shank 60 in position in a fixed angular position relative to the head 66. Many different conventional bone screws where the head locks relative to the shank are well known in the art.

The present invention is not intended to be restricted to a particular type of bone screw. In the present embodiment, a polyaxial type bone screw 6 is utilized wherein the shank 60 is locked in position by direct contact with the rod 4. It is foreseen that tool set 1 of the present invention can be used with virtually any type of bone screw, including polyaxial bone screws of many different types wherein the head is locked relative to the shank by structure other than in the manner described in the illustrated embodiment.

Each bone screw head 66 has a pair of upstanding arms 74 and 75 with internal second guide and advancement structure 76 on the insides thereof. One of the arms 74 includes a circumferentionally located receiver 78 that comprises a lower slot 79 that extends partially circumferentially about the periphery of the arm 74 and ends in an upwardly projecting but hidden recess 80. While the slot 79 is located on the arm 74 in the illustrated embodiment, a slot for this purpose could be located anywhere on the bone screw head 66. The slot 79 and recess 80 are sized, shaped and positioned so as to receive the attachment structure 55 of the end guides 9 therein. For greater detail, see the description below for the attachment structure associated with intermediate guide tools 10 and shown in FIGS. 10 and 11. The guide tool attachment structure 55 is sized and shaped to allow the attachment structure 55 to be received in the receiver 78 and locked therein by pulling the end guide tool 9 slightly axially upward relative to a respective bone screw 6. In order to disengage the guide tool 9 from the bone screw 6, the guide tool 9 is rotated 90 degrees counterclockwise from an attaching configuration, when viewing from the top so as to disengage the hook 57 from the recess 80 and so that the base 56 and hook 57 of the attachment structure 55 free to rotate above the rod 4 and closure top 52 and be released from the receiver 78. In this manner, end guide tools 9 twist off of respective bone screws 6 and in the particular illustrated embodiment the end guide tools 9 are also assembled on the bone screws 6 by the opposite twist on maneuver is the reverse of the twist off maneuver. In certain embodiments where there is enough flexibility in the legs 53 and 54, such that the legs 53 and 54 can be splayed radially outwardly at the bottom 39 thereof in the manner shown in FIG. 7, so the end guide tool 9 snaps-on over the bone screw 6, as will be described for the intermediate guide tools 10 below.

The unflexed space between the legs 53 and 54 that is equivalent to the width of the opening 35 is preferably substantially equivalent to the space between the bone screw arms 74 and 75 so that the channel 34 of the end guide tool 9 aligns with the channel 67 of the bone screw 6 when the end guide tool 9 is mounted on a respective bone screw 6. The recess 49 is sized, shaped and positioned so that when the rod 4 is located in the bone screws 6, the end guide tool 9 can rotate about axis A and the recess 49 allows the end guide tool 9 to straddle over the rod 4, thereby allowing the end guide tool 9 to twist relative to the bone screw 6 and free the attachment structure 55 from the receiver 78 and thereafter be removed after all procedures are complete, as described below.

Each of the intermediate guide tools 10 (see especially FIGS. 1 to 3) have a somewhat similar overall shape when compared to the end guide tools 9 in that both are preferably of the same axial length and width and also have much structure in common; however with certain differences as noted. Many of the structures of the intermediate guide tools 10 that are the same as the end guide tools 9 are given the same reference number and the above noted description applies to each such tool 9 or 10.

Each intermediate guide tool 10 has an overall elongate body 84 with an upper portion 86, an intermediate portion 87 and a lower portion 88. In the upper portion 86, the body 84 is generally C-shaped having a radially outward opening and elongate and axially extending channel 90 terminating in a web or rear wall 91 with side walls 92 and 93. The channel 90 has a front opening 95 that extends parallel to an axis of the body 84 and that is sized and shaped to receive tools and elements described below.

The intermediate portion 87 also includes an outwardly opening channel 97 with a rear web or wall 98 having a lower end 100 and a front opening 99 that is not as wide as the opening 95. The lower portion 88 includes two spaced side walls or legs 93 and 94 with an elongate and axially extending passthrough opening 101 between the legs 93 and 94 that extends more than half way along the intermediate tool 10 and near the intermediate portion 87. The legs 93 and 94 define between them a pass through and aligned slot 105 sized and shaped to slidingly receive the rod 6.

The lower portion 88 extends substantially axially along the intermediate guide tools 10 and preferably to the location in use where the intermediate guide tools 10 pass through the skin 14.

The bottom 39 of each intermediate guide tool 10 includes a helically wound but discontinuous square thread or first guide and advancement structure 109 that cooperates with the closure top 52, as described below. The lower end of each intermediate guide tool 10 also includes a cutout 112 and an attachment structure 113 similar to structure 55 of the same type described for each end guide tool 9.

The attachment structure 113 (see especially FIGS. 9 to 11) includes a body 114 with an upwardly extending, projection, flange or hook member 115 that follows the inner curvature of the guide tool leg 93. The body 114 extends radially inward and is sized and shaped to mate with and set within the bone screw head receiver 78. The bone screw receiver 78 is sufficiently wide to simultaneously receive both the body 114 and hook member 115 in a radially inward direction, as is shown in the view in FIG. 10. The attachment structure 113 is then set by axially raising the guide tool 10 relative to the bone screw 6 so at least part of the hook member 115 is located in the recess 80 which secures the guide tool 10 (likewise guide tool 9) to a respective bone screw 6, as seen in FIG. 11. This locks the guide tool 10 to a respective bone screw 6 and prevents outward splaying of the leg 93. This is a snap-on type installation or assembly as seen in FIG. 7 where the leg 93 splays outward during initial placement of the guide tool 10 over the bone screw 6 and then returns to an unsplayed position when the attachment structure 113 seats in the receiver 78, as shown in FIG. 10. Alternatively, the guide tool 10 can be rotated approximately 90.degree. about its axis A prior to joining with a respective bone screw 6, the attachment structure 113 lowered through the opening between the bone screw arms 74 and 75 and aligned with the bone screw receiver 78, after which the guide tool 10 is rotated back to the first position shown in FIG. 11 in a twist on type assembly. In some instances the guide tool 10 is rotated somewhat more or less than ninety degrees to make the necessary alignment for removal which depends on the specific construction of the parts.

Enclosure 52 closes between the spaced bone screw arms 74 and 75 to secure the rod 4 in the channel 67. The closure top 52 can be any of many different plug type closures. Preferably the closure top 52 has a cylindrical body 123 that has a helically wound mating guide and advancement structure 125. The guide and advance at structure 125 can be of any type, including V-type threads, buttress threads, reverse angle threads, or square threads. Preferably the guide and advancement structure 125 is a helically wound flange form that interlocks with a reciprocal flange form as part of the second guide and advancement structure 76 on the interior of the bone screw arms 74 and 75. A suitable locking guide and advancement structure of this type is disclosed in U.S. Pat. No. 6,726,689 from Ser. No. 10/236,123 which is incorporated herein by reference. The helical wound guide 50 and advancement structure in the bottom 39 of each of the guide tools 9 and 10 is sized and shaped to receive the mating guide and advancement structure 125 of the closure top 52 and align with the second guide and advancement structure 76 of the bone screw 6 to form a generally continuous helically wound pathway, but does not require locking between the closure top 52 and the tools 9 and 10, even when a locking flange form is utilized on the closure top 52. The illustrated structure 125 has a square form or a square thread type shape. The guide 50 allows the closure top 52 to be rotated and the surgeon to develop mechanical advantage to urge or drive the rod 4, while still outside the bone screw head 6, toward and into the bone screw head 66. This is especially helpful where the rod 4 is bent relative to the location of the vertebra 18 to which the rod 4 is to attach and is not easily placed in the bone screw head 66 without force and the mechanical advantage provided by the guide 50. In particular, the first guide and advancement structure 109 on each tool 9 and 10 is located and positioned to align with the second guide and advancement structure 76 on the insides of the bone screw arms 74 and 75, as seen in FIGS. 17 and 18 and pass the closure top 52 therebetween while allowing the closure top 52 to continue to rotate and to continuously apply force to the rod 4, so as to seat the rod 4 in the bone screw head 66.

Each closure top 52 also preferably includes a break off head 127 that breaks from the body 123 in a break off region 128 upon the application of a preselected torque, such as 95 inch-pounds. The break off head preferably has a hexagonal cross section faceted exterior 129 that is adapted to mate with a similarly shaped socket of a closure driving or installation tool 145, described below. It is foreseen that different driving heads or other methods of driving the closure top 52 can be utilize with certain embodiments of the invention.

Additional tools are utilized to assemble the implant. In particular, FIG. 16 illustrates a rod pusher 136 on the left. The pusher 136 has an elongate shaft or rod 138 that is preferably received in and passes through the interior of the guides 9 and 10, such as the channel 90 of the guide tool 10. The pusher 136 also has a tip 139 for engaging and urging the rod 4 downward, where there is minor resistance, and a handle 141. It is foreseen that a pusher or gripper of the type that operates outside the guide tools 9 and 10 can be utilized, but is not preferred as such would normally require greater penetration of the skin 14 and more invasion of the patient.

Shown in FIG. 16 on the left and in FIG. 17 is the closure installation tool 145. The tool 145 has an elongate rod or shaft 147 adapted to be received in and pass axially through any of the channels of the guides 9 and 10 and a handle 149. The lower end of the rod 147 terminates in a socket 148 that is adapted to receive the closure break off head 127, as shown in FIG. 17.

Another tool used in implanting a rod 4 is an antitorque tool 153 which is seen in FIGS. 20 to 22. The antitorque tool 153 is preferably used with the closure installation tool 145 to torque and set the closure top 52, so it is snug against the rod 4, and thereafter break away the break off head 127 in the manner shown in FIG. 22. The antitorque tool 153 includes a tubular hollow shaft 155 that is sized and shaped to be slidably received over the guide 9 and 10. The antitorque tool 153 has a lower end 157 that has a pair of diametrically spaced bridges 158. Each of the bridges 158 is sized and shaped to fit over the rod 4, as seen in FIG. 21. When in place, as seen in FIG. 21, the antitorque tool 153 allows a surgeon to counter torque applied by the installation tool 145, when applying torque to and breaking away the break off head 127. The antitorque tool 153 also has an upper handle 16 with an opening through which the installation tool 145 passes in the manner suggested by the dashed lines in FIG. 20.

In use, the previously described tools are utilized to attach one or more rods 4 to the human spinal column 17.

The procedure is begun by forming a relatively small incision, such as incision 165 in the skin 14 for each bone screw 6 to be used. The incisions 165 are stretched into a round shape with a circumference equal to or just slightly larger than the guide tools 9 and 10. The skin 14 is relatively flexible and allows the surgeon to move the incision 165 around relative to the spine 17 to manipulate the various tools and implants, as required. A drill (not shown) is utilized to form a guide bore (not shown) in a vertebra 18 under guidance of non invasive imaging techniques, which procedure is well known and established. A thin pin 166 is inserted in the guide bore. A bone screw 6 is selected in accordance with the size of the patient's vertebra 18 and the requirements of the spinal support needed. Bone screws 6 having a rotatable or poly axial head 66 are preferred for the procedure, as such allow relatively easy adjustment of the rod 4 in the tools 9 and 10 during placement and for movement of tools 9 and 10, as described below. The bone screw 6 is also cannulated so as to be receivable over and guided by the pin 166 toward the proper position in the associated vertebra 18.

Before placing the bone screw 6 in the vertebra 18, the bone screw 6 is preferably joined to an associated guide tool 9 or 10. This could be done after insertion of the bone screw 6, but it is preferred to assemble both before inserting the bone screw 6. With respect to the intermediate guide tool 10, the lower end of the guide tool 10 is splayed or expanded outwardly by forcing the bone screw head 66 between the legs 93 and 94, in the manner shown in FIG. 7 until the attachment structure 113 aligns with the receiver 78 and the former snaps into the later, as shown in FIG. 8. Axial upward movement of the guide tool 10 relative to the bone screw 6 then sets the attachment structure 113 in the recess 80 in the process that is illustrated between FIGS. 10 and 11. Alternatively, the tool 10 can be axially rotated ninety degrees relative to the bone screw 6 and the attachment structure 113 aligned with the recess 80 and then rotated back. The placement of the guide tools 9 on the associated bone screws 6 normally follows the later twist on procedure, as the structure of the guide tools 9 allow less flexing because of the longer back wall 21. With tool 9, the attachment structure 55 is placed in a respective receiver 55.

A series of bone screws 6 are installed in each vertebra 18 to be attached to the rod 4 by use of a screwdriver or installation tool 135, see FIG. 12, that has a head, designed to grip the particular bone screw 6 used and which is also cannulated to receive the pin 166. For each bone screw 6, an associated guide tool 9 or 10 extends through the skin 14, as seen in FIG. 13. An end guide tool 9 is located at each end of the series of bone screws 6 and an intermediate guide tool 10 is located on each, intermediate bone screw 6. The end guide tools 9 are turned or rotated so the channels 34 therein face one another and the intermediate guide tools 10 are aligned so slots 105 align with the channels 34.

The rod 4 is then inserted diagonally through one of the end skin incisions 165 in the manner shown in FIG. 13 so that a first rod end 42 passes through the slots 105 in any intermediate guide tools 10 and into the channel 34 of the opposed end guide tool 9. Back muscle tissue separates easily here to allow the upper insertion of the rod 4 and can be further separated by finger separation or cutting through one of the incisions 165, if required.

After initial insertion, the second end 42 of the rod 4 is positioned in the channel 34 of the end guide tool 9 that is located next to the insertion point of the rod 4, as is seen in FIG. 14.

Once the rod 4 is positioned in the guide tools 9 and 10, a pusher tool 136 of the type shown in FIG. 16 is utilized to push the rod 4 in each guide tool 9 or 10 toward the bone screw 6 associated with the guide tool 9 or 10 until the rod 4 is in approximately the position seen in FIG. 15. During this time, the end guide tools 9 can be manipulated to help movement of the rod 4 therealong and can especially have the tops thereof splayed outwardly relative to each other, as seen in FIG. 15. Again, the flexibility of the skin 14 allows such manipulation. Once the rod 4 reaches the bottom 39 of the end guide tools 9, the rod ends 42 encounter the cut outs 45 on either side of the rod 4 and pass therethrough. The rod 4 is sized to extend a little beyond each end bone screw 6 to ensure full capture and reduce likelihood of dislodgement. Because the channels 34 are slightly inward of the full outer length of the rod 4, the channels 34 must be tilted outward somewhat as seen in FIG. 15 to allow the rod 4 to pass down the channels 34 or one end 42 must be driven downward before the other. When the rod 4 is at the bottom of the guide tools 9 and 10, such as seen in FIG. 19, the end guide tools 9 can be returned to a position that is appropriate for properly aligning the bone screw heads 6 relative to the rod 4 prior to tightening and torquing the closure tops 52. Because the rod 4 is normally bent and/or the vertebrae 18 do not align properly, the rod 4 must normally be biased into the bone screw heads 6. This is accomplished by using the closure installation tool 145 in the manner illustrated on the right hand side in FIG. 16 and in FIG. 17.

In particular, the tool 145 has a socket 148 that grips the break off head 127 of the closure top 52. The installation tool 145 with closure top 52 therein is placed in the elongate top to bottom channel associated with the guide tools 9 and 10 either by entry from the side such as into channel 25 through opening 26 in guide tool 9 or into channel 25 through the top end 38 of the guide tool 9. The closure top 52 is then driven under manual control of the surgeon by use of the installation tool 145 toward the rod 4. Near the bottom of the guide tools 9 and 10, such as near the bottom 39 of end guide tool 9, the closure top 52 engages the helical wound first guide and advancement structure 50 and the tool 145 and closure top 52 are rotated mate the closure top helical mating structure 125 with the first guide and advancement structure 50 so as to drive the closure top 52 downward against the rod 4 and to urge the rod 4 downward into the bone screw channel 67. At the bottom of the guide tool 9 or 10, the closure top mating structure 125 engages and begins to mate with the guide and advancement structure 76 on a respective bone screw 6 and continued rotation of the tool 145 drives the rod 4 downward and into engagement with the dome 71 of the bone screw shank 60, so as to snug against and frictionally lock the shank 60 in position relative to the bone screw head 66, see FIG. 18.

Once all of the closure tops 52 are in final seating position in respective bone screws 6 and the surgeon is satisfied with the position of all of the elements, such as is seen in FIG. 19, the antitorque tool 153 is mounted over each guide tool 9 or 10, as shown in FIG. 21 with the bridges 158 straddling the rod 4 to prevent rotation. The installation tool 145 is inserted in the associated guide tool 9 or 10 and engaged with the break off head 127. By cooperative use of the tools 145 and 153 a preselected torque is manually applied to the break off head 127 and it breaks from the closure top body 123 in the manner shown in FIG. 22 and is removed along with the antitorque tool 153.

The guide tools 9 and 10 are then each rotated ninety degrees to align the attachment structure, such as structures 55 and 113 with the opening between bone screw arms 74 and 75, as shown in FIG. 23, so that the recess 49 straddles the rod 4 to allow the attachment structure 55 or 113 to disengage from the receiver 78. The guide tool 9 or 10 is then pulled axially upward away from the bone screw 6 and from the incision 165 in the skin 14, after which the incision 165 is closed.

It is to be understood that while certain forms of the present invention have been illustrated and described herein, it is not to be limited to the specific forms or arrangement of parts described and shown.

The invention claimed is:

1. A bone anchor to anchor an elongated implant to a patient bone and threadably engage with a closure plug, the bone anchor further to couple with a tool comprising an attachment structure, the bone anchor comprising:
    an anchoring member comprising a distal portion and a proximal portion opposite the distal portion, the distal portion to attach to the patient bone in an anchoring manner; and
    a head coupled to the proximal portion of the anchoring member, the head to couple to the elongated implant, the head comprising:
        a proximal end and a distal end opposite the proximal end, the proximal portion of the anchoring member extending into the distal end such that the head is coupled to the proximal portion of the anchoring member;
        a first arm and a second arm spaced apart from the first arm to define a channel to receive the elongated implant to couple the head to the elongated implant, the channel extending distally from the proximal end;
        a helically wound thread defined in an inner surface of the channel, the inner surface facing radially inward towards a longitudinal center axis of the head, the helically wound thread to threadably engage with the closure plug when the closure plug is received in the channel;
        an outer surface facing radially outward relative to the longitudinal center axis of the head, the outer surface being on the first arm; and
        a horizontal radiused slot near the proximal end of the head and extending along at least a portion of the outer surface in a direction perpendicular to the longitudinal center axis of the head, the slot to receive the attachment structure when the bone anchor is coupled to the tool; and
    wherein the horizontal radiused slot comprises a proximal boundary comprising a radially inner extent and a radially outer extent radially outward of the radially inner extent, wherein the radially outer extent is distal the radially inner extent.

2. The bone anchor of claim 1, wherein, when the bone anchor is coupled to the tool, a free end of the attachment structure is received in a proximal recess defined by the radially inner extent and the radially outer extent.

3. The bone anchor of claim 2, wherein the free end and the radially outer extent interact to inhibit the attachment structure from radially outward displacement.

4. A bone anchor to anchor an elongated implant to a patient bone and threadably engage with a closure plug, the bone anchor further to couple with a tool comprising an attachment structure, the bone anchor comprising:
    an anchoring member comprising a distal portion and a proximal portion opposite the distal portion, the distal portion to attach to the patient bone in an anchoring manner; and
    a head coupled to the proximal portion of the anchoring member, the head to couple to the elongated implant, the head comprising:
        a proximal end and a distal end opposite the proximal end, the proximal portion of the anchoring member extending into the distal end such that the head is coupled to the proximal portion of the anchoring member;
        a first arm and a second arm spaced apart from the first arm to define a channel to receive the elongated implant to couple the head to the elongated implant, the channel extending distally from the proximal end;
        a helically wound thread defined in an inner surface of the channel, the inner surface facing radially inward towards a longitudinal center axis of the head, the helically wound thread to threadably engage with the closure plug when the closure plug is received in the channel;
        an outer surface facing radially outward relative to the longitudinal center axis of the head, the outer surface being on the first arm; and
        a horizontal radiused slot near the proximal end of the head and extending along at least a portion of the outer surface in a direction perpendicular to the longitudinal center axis of the head, the slot to receive the attachment structure when the bone anchor is coupled to the tool; and
    wherein the horizontal radiused slot comprises a proximal boundary comprising a distal projecting lip structure and, when the bone anchor is coupled to the tool, the attachment structure engages the distal projecting lip.

5. The bone anchor of claim 4, wherein the attachment structure engaging the distal projecting lip acts to inhibit the attachment structure from radially outward displacement.

6. A bone anchor to anchor an elongated implant to a patient bone and threadably engage with a closure plug, the bone anchor further to couple with a tool comprising an attachment structure, the bone anchor comprising:

an anchoring member comprising a distal portion and a proximal portion opposite the distal portion, the distal portion to attach to the patient bone in an anchoring manner; and a head coupled to the proximal portion of the anchoring member, the head to couple to the elongated implant, the head comprising:

a proximal end and a distal end opposite the proximal end, the proximal portion of the anchoring member extending into the distal end such that the head is coupled to the proximal portion of the anchoring member;

a first arm and a second arm spaced apart from the first arm to define a channel to receive the elongated implant to couple the head to the elongated implant, the channel extending distally from the proximal end;

a helically wound thread defined in an inner surface of the channel, the inner surface facing radially inward towards a longitudinal center axis of the head, the helically wound thread to threadably engage with the closure plug when the closure plug is received in the channel;

an outer surface facing radially outward relative to the longitudinal center axis of the head, the outer surface being on the first arm; and a horizontal radiused slot near the proximal end of the head and extending along at least a portion of the outer surface in a direction perpendicular to the longitudinal center axis of the head, the slot to receive the attachment structure when the bone anchor is coupled to the tool;

wherein the slot comprises a boundary perpendicular to the longitudinal center axis of the head that comprises a structural configuration that interacts with the attachment structure to inhibit radially outward displacement of the attachment structure from the slot in which the attachment structure is received; and wherein the structural configuration comprises a lip structure.

7. The bone anchor of claim 6, wherein the boundary perpendicular to the longitudinal center axis of the head is a proximal boundary.

8. A bone anchor to anchor an elongated implant to a patient bone and threadably engage with a closure plug, the bone anchor further to couple with a tool comprising an attachment structure, the bone anchor comprising:

an anchoring member comprising a distal portion and a proximal portion opposite the distal portion, the distal portion to attach to the patient bone in an anchoring manner; and a head coupled to the proximal portion of the anchoring member, the head to couple to the elongated implant, the head comprising:

a proximal end and a distal end opposite the proximal end, the proximal portion of the anchoring member extending into the distal end such that the head is coupled to the proximal portion of the anchoring member;

a first arm and a second arm spaced apart from the first arm to define a channel to receive the elongated implant to couple the head to the elongated implant, the channel extending distally from the proximal end;

a helically wound thread defined in an inner surface of the channel, the inner surface facing radially inward towards a longitudinal center axis of the head, the helically wound thread to threadably engage with the closure plug when the closure plug is received in the channel;

an outer surface facing radially outward relative to the longitudinal center axis of the head, the outer surface being on the first arm; and a horizontal radiused slot near the proximal end of the head and extending along at least a portion of the outer surface in a direction perpendicular to the longitudinal center axis of the head, the slot to receive the attachment structure when the bone anchor is coupled to the tool;

wherein the proximal end comprises a surface perpendicular to the outer surface:

wherein the horizontal radiused slot is closer in proximity to the proximal end than to the distal end; and wherein a proximal perpendicular boundary of the horizontal radiused slot comprises an undercut defining a proximal projecting recess of the horizontal radiused slot.

9. The bone anchor of claim 8, wherein the recess of the slot is to interact with the attachment structure to prevent radially outward displacement of the attachment structure from the slot in which the attachment structure is received.

10. A bone anchor to anchor an elongated implant to a patient bone and threadably engage with a closure plug, the bone anchor further to couple with a tool comprising an attachment structure, the bone anchor comprising:

an anchoring member comprising a distal portion and a proximal portion opposite the distal portion, the distal portion to attach to the patient bone in an anchoring manner; and a head coupled to the proximal portion of the anchoring member, the head to couple to the elongated implant, the head comprising:

a proximal end and a distal end opposite the proximal end, the proximal portion of the anchoring member extending into the distal end such that the head is coupled to the proximal portion of the anchoring member;

a first arm and a second arm spaced apart from the first arm to define a channel to receive the elongated implant to couple the head to the elongated implant, the channel extending distally from the proximal end;

a helically wound thread defined in an inner surface of the channel, the inner surface facing radially inward towards a longitudinal center axis of the head, the helically wound thread to threadably engage with the closure plug when the closure plug is received in the channel;

an outer surface facing radially outward relative to the longitudinal center axis of the head, the outer surface being on the first arm; and a horizontal radiused slot near the proximal end of the head and extending along at least a portion of the outer surface in a direction perpendicular to the longitudinal center axis of the head, the slot to receive the attachment structure when the bone anchor is coupled to the tool; and wherein the horizontal radiused slot comprises a planar boundary perpendicular to the longitudinal center axis of the head and perpendicularly intersecting the outer surface.

11. The bone anchor of claim 10, wherein the planar boundary makes complementary planar surface contact with the attachment structure when the attachment structure is received in the slot.

12. The bone anchor of claim 10, wherein the planar boundary is located at a proximal region of the slot.

13. The bone anchor of claim 12, wherein the slot further comprises a recessed portion comprising another planar boundary perpendicular to the longitudinal center axis of the head, the another planar boundary being stepped proximally from the planar boundary and located radially inward from the planar boundary.

14. The bone anchor of claim 13, wherein the recessed portion interacts with the attachment structure in a manner that inhibits radially outward displacement of the attachment structure from the slot.

15. A bone anchor to anchor an elongated implant to a patient bone and threadably engage with a closure plug, the bone anchor further to couple with a tool comprising an attachment structure near a lower end of the tool, the bone anchor comprising:
   an anchoring member comprising a distal portion and a proximal portion opposite the distal portion, the distal portion to be attached to the patient bone in an anchoring manner; and
   a head to be coupled to and located near the proximal portion of the anchoring member and to couple to the elongated implant, the head comprising:
      a proximal region with a proximal end, and a distal region opposite the proximal end, the proximal portion of the anchoring member extending distally from the distal region of the head;
      a first arm and a second arm spaced apart from the first arm to define a channel therebetween to receive the elongated implant to couple the head to the elongated implant, the channel extending distally from the proximal end of the head;
      a helically wound thread defined in an inner surface on opposite sides of the channel, the inner surface facing radially inward towards a longitudinal center axis of the head, the helically wound thread to threadably engage with the closure plug when the closure plug is received in the channel;
      an outer surface facing radially outward relative to the longitudinal center axis of the head, the outer surface being on at least the first arm; and
      a horizontal radiused slot extending along at least a portion of the outer surface in a direction perpendicular to the longitudinal center axis of the head and radially spaced therefrom, the slot to receive the attachment structure when the bone anchor is coupled to the tool, the slot located near the proximal end of the head, and the proximal end of the head having a top surface thereon
   wherein the horizontal radiused slot comprises a recessed overhanging configuration at a proximal boundary of the horizontal radiused slot.

16. A bone anchor to anchor an elongated implant to a patient bone and threadably engage with a closure plug, the bone anchor further to couple with a tool comprising an attachment structure near a lower end of the tool, the bone anchor comprising:
   an anchoring member comprising a distal portion and a proximal portion opposite the distal portion, the distal portion to be attached to the patient bone in an anchoring manner; and
   a head to be coupled to and located near the proximal portion of the anchoring member and to couple to the elongated implant, the head comprising:
      a proximal region with a proximal end, and a distal region opposite the proximal end, the proximal portion of the anchoring member extending distally from the distal region of the head;
      a first arm and a second arm spaced apart from the first arm to define a channel therebetween to receive the elongated implant to couple the head to the elongated implant, the channel extending distally from the proximal end of the head;
      a helically wound thread defined in an inner surface on opposite sides of the channel, the inner surface facing radially inward towards a longitudinal center axis of the head, the helically wound thread to threadably engage with the closure plug when the closure plug is received in the channel;
      an outer surface facing radially outward relative to the longitudinal center axis of the head, the outer surface being on at least the first arm; and
      a horizontal radiused slot extending along at least a portion of the outer surface in a direction perpendicular to the longitudinal center axis of the head and radially spaced therefrom, the slot to receive the attachment structure when the bone anchor is coupled to the tool, the slot located near the proximal end of the head, and the proximal end of the head having a top surface thereon
   wherein the horizontal radiused slot comprises a proximal boundary comprising a radially inner extent and a radially outer extent radially outward of the radially inner extent, wherein the radially outer extent is distal the radially inner extent.

17. The bone anchor of claim 16, wherein, when the bone anchor is coupled to the tool, a free end of the attachment structure is received in a proximal recess defined by the radially inner extent and the radially outer extent.

18. The bone anchor of claim 17, wherein the free end and the radially outer extent interact to inhibit the attachment structure from radially outward displacement.

19. The bone anchor of claim 15, wherein the bone screw is a polyaxial bone screw.

* * * * *